United States Patent [19]

Harris et al.

[11] 4,391,677
[45] Jul. 5, 1983

[54] PROCESS FOR PRODUCING SUBSTANTIALLY SULPHUR-FREE BUTENE-1

[75] Inventors: Norman Harris, Stockton-on-Tees, England; John F. Flintoff, Thousand Oaks, Calif.; John W. Kippax, Stockton on Tees, England

[73] Assignee: Davy McKee (Oil & Chemicals) Limited, London, England

[21] Appl. No.: 296,873

[22] Filed: Aug. 27, 1981

Related U.S. Application Data

[63] Continuation of Ser. No. 132,293, Mar. 20, 1980, abandoned.

[30] Foreign Application Priority Data

Mar. 21, 1979 [GB] United Kingdom ................. 7910010
Nov. 28, 1979 [EP] European Pat. Off. ........ 79302707.9

[51] Int. Cl.³ .............................................. B01D 3/14
[52] U.S. Cl. ...................................... 203/28; 203/41
[58] Field of Search ...................... 203/41, 29, 31, 32, 203/28; 585/809, 820, 822, 823, 824; 55/73–75; 210/24, 26, 35, 502; 62/18

[56] References Cited

U.S. PATENT DOCUMENTS 2,768,942 10/1956 Marple et al. ........................ 203/41
2,818,458 12/1957 Harclerode et al. .................... 62/18

*Primary Examiner*—Frank Sever
*Attorney, Agent, or Firm*—Bernard, Rothwell & Brown

[57] ABSTRACT

A process is disclosed for producing a substantially sulphur-free, butene-1 rich stream from a butene-containing $C_4$ hydrocarbon feed stream by passage through a desulphurization zone, e.g. successive beds of active alumina and zinc oxide, and then distilling it. The desulphurization zone adsorbs, absorbs or converts to higher boiling sulphurous compounds low boiling sulphurous impurities such as $H_2S$, COS and $CH_3SH$. A sulphur-free butene-1 rich stream is recovered overhead from the distillation zone, while a butene-2 rich stream containing higher boiling sulphurous impurities originally present or produced in the desulphurization zone is recovered as a bottom product. A dechlorination zone (containing, for example, a charge of copper impregnated active carbon) can be provided upstream or downstream from the desulphurization zone but upstream from the distillation zone or can be provided in the path of the butene-1 rich stream from the distillation zone. The butene-1 rich product is suitable for use as a hydroformylation feedstock.

13 Claims, 1 Drawing Figure

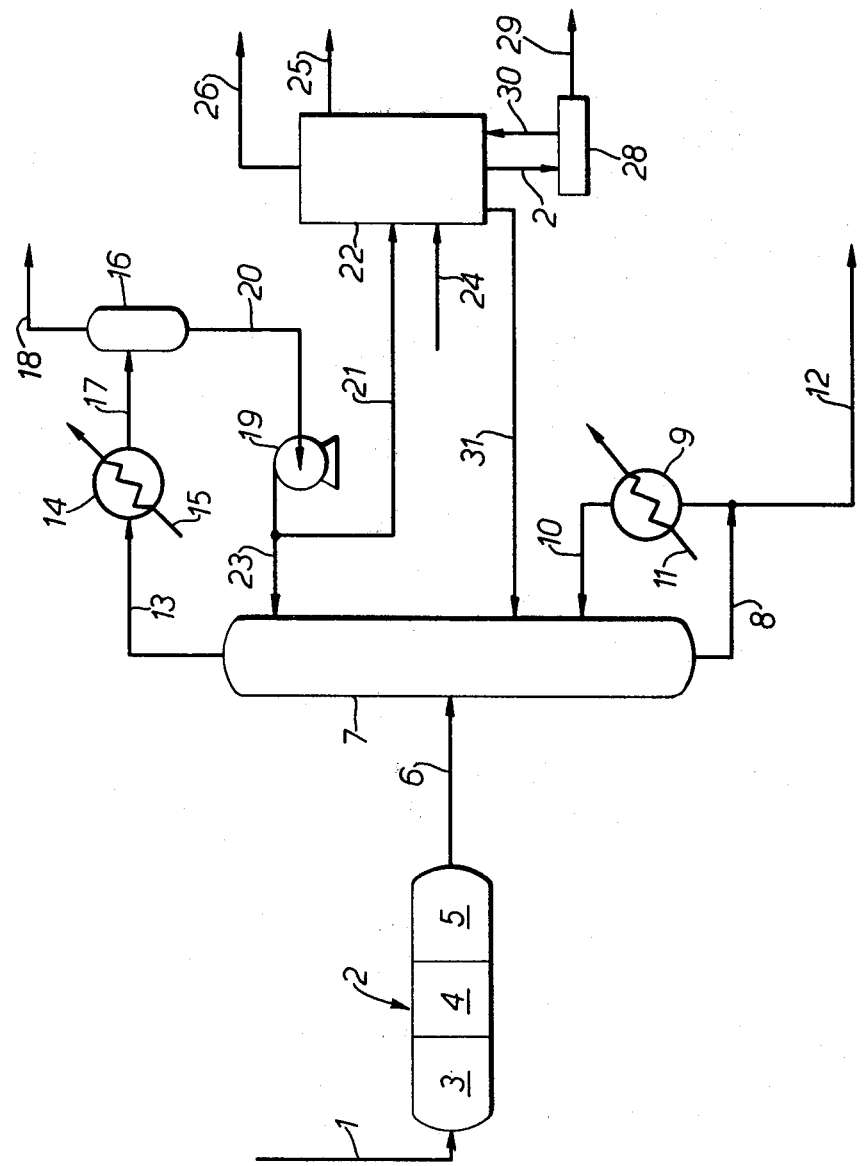

PROCESS FOR PRODUCING SUBSTANTIALLY SULPHUR-FREE BUTENE-1

This is a continuation of application Ser. No. 132,293 filed Mar. 20, 1980, abandoned.

This invention relates to a process for the treatment of butene-containing feed streams. More particularly it relates to the production from such a feed stream of a butene-1 rich stream suitable for hydroformylation.

Butene-containing feed streams are produced by a variety of high temperature and catalytic processes employing natural gas and petroleum fractions as feedstocks. Large amounts of such butene-containing materials are produced in refinery catalytic processes using the higher-boiling fractions of petroleum, such as gas oil. Typically such $C_4$ fraction feed streams contain butene-1 and cis- and trans-butene-2 in variable amounts, together with n-butane, iso-butane, butadiene, and iso-butylene. Additionally such $C_4$ fractions may contain as impurities minor amounts of sulphur compounds (e.g. $H_2S$, COS, mercaptans and/or sulphides) and/or halogen compounds.

Hydroformylation is a well-known technique for production of a $Cn+1$-aldehyde from a terminal $Cn$-olefin. Thus ethylene can be reacted with an approximately 1:1 $CO:H_2$ mixture in the presence of a suitable catalyst to form propionaldehyde and propylene can be similarly reacted to form butyraldehyde. The aldehyde products formed in this way can then be hydrogenated to the corresponding alcohol (e.g. propanol or butanol) or aldolised, dehydrated and reduced to form plasticiser alcohols (e.g. 2-ethyl-hexanol from butyraldehyde). Such hydroformylation techniques include, for example, the rhodium-catalysed process described in United Kingdom patent specification Nos. 1,197,847 and 1,338,237 and commercial plants employing this technique for the hydroformylation of ethylene and propylene are already in operation in the United States and in Puerto Rico respectively.

Although terminal olefins, such as propylene, heptene-1 or butene-1, can readily be hydrofo mylated, internal olefins, such as cis- and trans-butene-2, react very slowly under normal rhodium-catalysed hydroformylation conditions. Hence if a gas mixture containing butene-1 and cis- and trans-butene-2 is passed through a rhodium catalyst-containing hydroformylation zone under favourable conditions for the hydroformylation of the terminal olefin (butene-1), it has been found that the internal olefins (cis- and trans-butene-2) effectively behave as inert materials. Thus, in order to achieve efficient operation in a compact plant, it would be desirable so to treat a butene-containing, $C_4$ hydrocarbon feed stream as to produce a butene-1 rich stream with a low butene-2 content. Furthermore, since sulphur compounds and, to a lesser extent, halogen compounds have been found to be undesirable components of feed streams to be used in rhodium-catalysed hydroformylation reactions, it would be desirable to produce a butene-1 rich stream that is essentially free from such compounds, and particularly from sulphur compounds.

The invention accordingly seeks to provide a process for the production in a simple and economic manner of a butene-1 rich stream that is essentially free from sulphurous impurities and that is suitable for use as a feedstock for the rhodium-catalysed production of n-valeraldehyde by hydroformylation of butene-1.

According to the present invention there is provided a process for the production of a substantially sulphur-free, butene-1 rich stream from a butene-containing $C_4$ hydrocarbon feed stream containing a minor amount of at least one compound selected from hydrogen sulphide, carbonyl sulphide, methyl mercaptan and high boiling sulphurous compounds, which process comprises passing the feed stream through a desulphurization zone maintained under desulphurization conditions and containing a charge of at least one desulphurization medium capable of adsorbing, absorbing or converting to high boiling sulphurous compounds hydrogen sulphide, carbonyl sulphide, and methyl mercaptan, passing thus-treated feed stream, now essentially free from hydrogen sulphide, carbonyl sulphide, and methyl mercaptan to a distillation zone, and recovering as a bottom product from the distillation zone a butene-2 rich stream containing high boiling sulphurous compounds and as an overhead product from the distillation zone a substantially sulphur-free, butene-1 rich stream.

Preferably the process includes a dechlorination step which may be effected either upstream or downstream from either the desulphurization zone or the distillation zone. Hence the process may include the step of passing the butene-1 rich stream or the feed stream (either before or after passage through the desulphurization zone) through a dechlorination zone thereby to remove substantially all of any chlorine-containing impurities. Conveniently the dechlorination zone is downstream from the desulphurization zone and upstream from the distillation zone.

The amount and nature of the sulphurous impurities in the $C_4$ hydrocarbon feed stream depend on the source of the feed stream and subsequent treatment thereof. For example, the $C_4$ hydrocarbon feed stream, depending on its origin, may contain from about 1 ppm sulphur or less up to about 100 ppm sulphur or more. Usually the feed stream will contain from about 2 ppm sulphur up to about 25 ppm sulphur. Among possible sulphurous impurities there can be mentioned hydrogen sulphide ($H_2S$), carbonyl sulphide (COS) and methyl mercaptan ($CH_3SH$), as well as high boiling sulphurous impurities, such as carbon disulphide ($CS_2$) and dimethyl sulphide ($CH_3SCH_3$). The desulphurization zone is designed so as to be suitable for the removal, or for the conversion to high boiling sulphurous compounds, of the light sulphurous impurities hydrogen sulphide, carbonyl sulphide, and methyl mercaptan. The feed stream after passage through the desulphurization zone is essentially free from hydrogen sulphide, carbonyl sulphide and methyl mercaptan and now contains, as significant sulphurous impurities, only high boiling impurities such as dimethyl sulphide. This means that the design of the desulphurization zone is simple since it needs only to be designed for removal of the low boiling sulphurous impurities and removal of the high boiling sulphurous impurities such as dimethyl sulphide and carbon disulphide can be achieved in the distillation zone, such remaining high boiling sulphurous impurities appearing in the butene-2 rich bottom product stream.

The feed stream, prior to passage through the desulphurization zone, may be gaseous but preferably is liquid.

The desulphurization zone may be maintained at a temperature in the range of from 0° C. or below up to 200° C. or more. The pressure may range from atmospheric pressure up to about 40 atmospheres or more, or it may be subatmospheric. Usually it will be preferred to maintain a superatmospheric pressure in the desulphurization zone. It will usually be preferred to operate the desulphurization zone at a temperature in the range of from about 0° C. to about 40° C. Under these conditions the feed stream can be efficiently freed from hydrogen sulphide and carbonyl sulphide by contact in liquid form with a suitable desulphurization medium or media. If desired, however, the desulphurization zone can be operated at higher temperatures, e.g. in the range of from about 180° C. to about 200° C., with the feed stream in gaseous form. In this case the feed stream can be heated prior to passage through the desulphurization zone.

A suitable desulphurization procedure involves passage of the feed stream, whether in liquid or gaseous form, through an active alumina bed and then through a zinc oxide bed. We have found that, under suitable conditions and in the absence of free molecular oxygen, the active alumina bed functions to hydrolyse carbonyl sulphide to hydrogen sulphide and partially to remove hydrogen sulphide and methyl mercaptan. The zinc oxide then removes essentially all the hydrogen sulphide and methyl mercaptan that is not removed by the active alumina. However, when the feed stream contains free molecular oxygen, some conversion of methyl mercaptan to dimethyl sulphide is generally found to occur in the desulphurization zone. Since the desulphurization zone is followed by the distillation zone and since such dimethyl sulphide is removed in the butene-2 rich bottom product fraction from the distillation, such formation of dimethyl sulphide in the desulphurization zone is not disadvantageous.

In order to enable the hydrolysis mentioned in the previous paragraph to occur the presence of water in the feed stream is essential. The amount of water is not critical and amounts of, for example, about 20 ppm up to about 1000 ppm or more are usually sufficient. If the feed stream does not already contain water then a small amount of water can be added to the feed stream.

After passage through the desulphurization zone the feed stream is now substantially free from hydrogen sulphide, carbonyl sulphide and methyl mercaptan, but still possibly contains high boiling sulphurous impurities, such as dimethyl sulphide.

The various $C_4$ hydrocarbons have different physical properties. In particular the boiling point of butene-1 at 760 mm Hg ($-6.26°$ C.) differs from those of cis-butene-2 ($+3.72°$ C.), trans-butene-2 ($+0.88°$ C.), n-butane ($-0.50°$ C.), iso-butane ($-11.73°$ C.) and butadiene ($-4.41°$ C.), although being close to that of iso-butylene ($-6.90°$ C.). Hence it is a relatively simple matter to design the distillation zone such that a butene-1 rich fraction (containing substantially all of any butene-1 together with any iso-butane and iso-butylene present) can be separated as an overhead fraction from a butene-2 rich bottoms product that contains substantially all the cis- and trans-butene-2 present in the feed stream.

The butene-containing, $C_4$ hydrocarbon feed stream, after passage through the desulphurization zone, is fed to the distillation zone at a suitable pressure and temperature either as a liquid or in vapour form. Generally the pressure in the distillation zone ranges from atmospheric pressure up to 35 atmospheres absolute, typically in the range of from 5 atmospheres absolute up to 30 atmospheres absolute. It is not practicable to operate much above 35 atmospheres absolute because the critical pressure of the various unsaturated $C_4$ hydrocarbons all lie in the region of 40 atmospheres. The temperature of the feed to the distillation zone may range from below 0° C., e.g. $-20°$ C. or less, up to about 140° C. Since the critical temperatures of the various unsaturated $C_4$ hydrocarbons lie in the range of about 145° C. to 155° C. it is not practicable to operate the distillation zone at temperatures above about 140° C. Usually the temperature ranges from about $-10°$ C. up to about 40° C.

Since the feed stream to the distillation zone is essentially free from low boiling sulphurous impurities (i.e. hydrogen sulphide, carbonyl sulphide and methyl mercaptan) the overhead product, that is to say the butene-1 rich stream, is substantially sulphur free. Any high boiling sulphurous impurities present in the feed stream or produced in the desulphurization zone have boiling points above that of butene-1 and hence appear in the bottom product butene-2 rich stream.

The process may further include a dechlorination step. This can take place either before or after passage of the feed stream through the desulphurization zone. Alternatively the dechlorination step can be effected merely on the overhead product butene-1 rich stream from the distillation zone.

The amount and nature of the chlorinated impurities, if any, in the $C_4$ hydrocarbon feed stream depend on the origins and past history of the feed stream. Such chlorinated impurities may include low boiling impurities, such as, for example, hydrogen chloride (HCl) and methyl chloride ($CH_3Cl$), as well as high boiling chlorinated impurities, such as vinyl chloride ($CH_2$=CHCl).

The splitting that occurs in the distillation zone into butene-1 rich and butene-2 rich fractions also achieves a partial purification with respect to chlorinated impurities. Only low boiling chlorinated impurities such as hydrogen chloride and methyl chloride appear in the butene-1 rich fraction. Higher boiling chlorinated impurities such as vinyl chloride appear in the butene-2 rich stream.

If dechlorination is effected after the distillation step, it is only necessary to treat the butene-1 rich stream, which means that the only chlorinated impurities to be removed are low boiling ones, such as hydrogen chloride and methyl chloride. This means that the dechlorination procedure can be simple and that a relatively compact unit can be used since it is only the product stream that requires dechlorination. In turn this means that the chemicals requirements of the dechlorination unit are minimised.

The dechlorination zone may comprise a bed of any suitable dechlorination material, for example copper impregnated active carbon. The temperature in the dechlorination zone may range, for example, from about $-10°$ C. or below up to about 200° C. or more. However, if the stream to be dechlorinated is in liquid form it will usually be convenient to operate at temperatures in the range of from about 0° C. to about 100° C. Dechlorination of the stream in gaseous form will usually require more elevated temperatures, for example in the range of from about 40° C. to about 200° C.

The desulphurization zone and any dechlorination zone will usually conveniently be operated at essentially the same pressure as the distillation zone, allowing for the usual pressure drop, but can, if desired, be operated at some other pressure. In this latter case appropriate facilities must be provided between the zones for pressure adjustment (increase or decrease).

The bottom product from the distillation column contains substantially all of the heavy boiling sulphurous and chlorinated impurities such as dimethyl sulphide and vinyl chloride in addition to cis- and trans-butene-2. This product is generally exported beyond the battery limits for use elsewhere in the chemical factory, e.g. for the production of butylate petroleum or methyl ethyl ketone.

The process of the invention is operable with essentially any butene-containing feed stream that contains at least, for example, about 30% v/v butene-1 up to 85% v/v butene-1 or more, e.g. up to 99% v/v butene-1.

The process of the invention may further include a hydrofining step for the removal of butadiene. This can be upstream of the distillation zone so that the entire feed stream is hydrofined. Alternatively it is possible to hydrofine solely the overhead product from the distillation zone in order to remove substantially all traces of butadiene from the butene-rich stream.

If desired, the process can also include an acid wash step for the removal of iso-butylene. This acid wash step is preferably effected upstream from the distillation zone, but may alternatively be effected on the butene-1 rich stream downnstream from the distillation zone. The presence of iso-butylene in the butene-1 rich fraction does not, however, cause any problem in any subsequent rhodium-catalysed hydroformylation step. Since any acid washing step is energy-expensive it may be preferred not to attempt to remove any iso-butylene from the butene-1 rich feed to the hydroformylation zone but rather to recover the iso-butylene downstream from the hydroformylation zone since essentially all the iso-butylene passes through such zone unchanged.

SHORT DESCRIPTION OF DRAWING

In order that the invention may be readily understood and carried into effect a form of plant utilizing the process of the invention will now be described with reference to the accompanying diagrammatic drawing which shows the flow sheet of the plant in simplified form.

Referring to the drawing, a liquid $C_4$ hydrocarbon feed stream containing approximately 8 ppm sulphur and 100 ppm water vapour is supplied at a rate of 280 kg moles/hr via conduit 1 at a pressure of 9 kg/cm$^2$ and at a temperature of 15° C. to a combined desulphurization-dechlorination zone 2 which consists of three beds 3, 4 and 5 in series. Bed 3 consists of active alumina, whereas bed 4 is of zinc oxide, and bed 5 is of copper-impregnated carbon, for example Girdler G32J catalyst, obtainable from Girdler Chemicals Inc., Louisville, Ky., U.S.A. Beds 3 and 4 serve to hydrolyse COS to $H_2S$ and to adsorb or absorb low boiling sulphurous impurities such as $H_2S$, or $CH_3SH$ and/or to convert such low boiling sulphurous impurities to high boiling impurities such as dimethyl sulphide, butyl mercaptans, methyl butyl sulphides, dibutyl sulphides and the like. Bed 5 acts to remove substantially all low boiling chlorinated impurities such as HCl, and methyl chloride.

From zone 2 the feed stream, which is now substantially free from hydrogen sulphide, carbonyl sulphide and methyl mercaptan, is passed via line 6 to splitter column 7. Column 7 is of conventional type and is provided with 108 distillation trays. A liquid bottom product stream is removed through line 8 and vaporized in a reboiler 9 for return to column 6 through line 10. Reboiler 9 is heated by steam supplied via line 11. 83 kg moles/hr of this liquid bottom product are removed via line 12. This stream contains substantially all of the high boiling sulphurous impurities such as dimethyl sulphide present in the feed stream, together with substantially all the high boiling chlorine-containing impurities, such as vinyl chloride.

An overhead butene-1 fraction is removed from splitter column 7 via line 13 and passed to condenser 14 which is supplied with cooling water via line 15. From condenser 14 the now liquid overhead product passes on to reflux drum 16 via line 17. Reference numeral 18 indicates a suitable vent to control build up of non-condensible components. Condensate is withdrawn from reflux drum 16 by means of reflux pump 18 and line 20. 220 kg moles/hr of condensate are passed on via line 21 to a hydroformylation plant for hydroformylation in accordance with the process described in United Kingdom patent specification Nos. 1,197,847 and 1,338,237. The remaining condensate is recycled to splitter column 7 via line 23 at a rate of 1485 kg moles/hr.

Hydroformylation plant 22 is supplied with synthesis gas (approximately 1:1 by volume $H_2$:CO) from a partial oxidation plant (not shown) via line 24. 186 kg moles/hr of n-valeraldehyde rich product is withdrawn from plant 22 via line 25. An overhead purge stream is removed via line 26 at a rate of 26 kg moles/hr in order to control build-up of inerts, such as nitrogen and butane, in the system. Part of the liquid catalyst containing liquid phase is withdrawn from plant 22 via line 27 to a "heavies removal" zone 28 for treatment therein to remove up to 1 kg moles/hr high boiling aldehyde condensation products, these being withdrawn via line 29. Regenerated catalytic reaction zone liquid is recycled to the hydroformylation plant via line 30. 23 kg moles/hr of a butene-rich fraction are recycled to splitter column 7 from hydroformylation plant 22 via line 31 in order to prevent build up of butene-2 within the hydroformylation plant 22.

The compositions of the various streams are given in the following Table.

TABLE

| Component | Line 1 | Line 6 | Line 12 | Line 21 | Line 25 | Line 31 |
|---|---|---|---|---|---|---|
| butene-1 mole % | 69.88 | 69.88 | 5.63 | 88.11 | 0.20 | 15.0 |
| cis-butene-2 mole % | 10.06 | 10.06 | 31.57 | 3.20 | 1.40 | 21.98 |
| trans-butene-2 mole % | 15.10 | 15.10 | 47.39 | 4.80 | 2.10 | 32.97 |
| iso-butylene mole % | 1.00 | 1.00 | 1.92 | 1.11 | 0.14 | 5.50 |
| n-butane mole % | 2.23 | 2.23 | 8.91 | 1.46 | 0.49 | 19.12 |
| iso-butane mole % | 1.06 | 1.06 | 1.90 | 1.00 | 0.09 | 3.53 |
| propane mole % | 0.13 | 0.13 | <0.01 | 0.32 | — | 1.50 |
| pentane mole % | 0.54 | 0.54 | 1.83 | <0.01 | — | — |
| n-valeraldehyde mole % | — | — | 0.82 | — | 91.90 | 0.38 |
| i-valeraldehyde mole % | — | — | 0.03 | — | 3.67 | 0.02 |
| water ppm | 100 | 100 | 300 | — | — | — |
| sulphur ppm | 8 | <1.0 | <3 | <0.1 | — | — |
| chlorine ppm | 4 | <0.5 | <1.5 | <0.1 | — | — |

Although the zone 2 has been described as a single zone it will usually be preferred to provide duplicate zones so that, when the charges of chemicals require to be replaced, the flow can be switched from one zone to the duplicate to maintain continuous operation.

We claim:

1. A process for the production of a substantially sulphur-free, butene-1 rich stream suitable for use as a hydroformylation feedstock from a butene-containing $C_4$ hydrocarbon feed stream containing a minor amount of at least one sulphurous component selected from hydrogen sulphide, carbonyl sulphide, methyl mercaptan and mixtures of at least one thereof with at least one higher boiling sulphurous compound, which comprises providing a desulphurization zone maintained under desulphurization conditions and containing a charge of at least one solid desulphurization medium capable of converting to higher boiling sulphurous compounds at least a portion of the hydrogen sulphide, carbonyl sulphide, and methyl mercaptan present in the feed stream and of absorbing or adsorbing substantially the remainder of any hydrogen sulphide, carbonyl sulphide and methyl mercaptan present in the feed stream, contacting the feed stream in the desulphurization zone with the solid desulphurization medium in the presence of from about 20 ppm up to about 1000 ppm water, passing thus treated feed stream, now essentially free from hydrogen sulphide, carbonyl sulphide and methyl mercaptan, but containing at least one higher boiling sulphurous compound, said at least one higher boiling compound having been produced in the desulphurization zone, to a distillation zone, recovering as a bottom product from the distillation zone a butene-2 rich stream containing said at least one higher boiling sulphurous compound, and recovering as an overhead product from the distillation zone a substantially sulphur-free, butene-1 rich stream.

2. A process according to claim 1, in which the desulphurization zone is maintained at a temperature in the range of from about 0° C. up to about 200° C.

3. A process according to claim 2, in which the desulphurization zone is maintained at a temperature in the range of from about 0° C. to about 40° C.

4. A process according to claim 1, in which the desulphurization zone contains a charge of active alumina.

5. A process according to claim 4, in which the desulphurization zone contains a charge of zinc oxide downstream in the path of the feed stream from the charge of active alumina.

6. A process according to claim 1, 2, 3, 4 or 5, in which the feed stream contains from about 20 ppm up to about 1000 ppm of water.

7. A process according to claim 6, which further includes the step of passing the feed stream, upstream or downstream from the desulphurization zone but upstream from the distillation zone, through a dechlorination zone containing a charge of a dechlorination material and maintained under dechlorination conditions.

8. A process according to claim 7, in which the dechlorination zone comprises a charge of copper-impregnated active carbon.

9. A process according to claim 8, in which the temperature in the dechlorination zone ranges from about $-10°$ C. up to about 200° C.

10. A process according to claim 6, which further includes the step of passing the overhead product stream from the distillation zone through a dechlorination zone containing a charge of dechlorination material and maintained under dechlorination conditions.

11. A process according to claim 10, in which the dechlorination zone comprises a charge of copper-impregnated active carbon.

12. A process according to claim 11, in which the temperature in the dechlorination zone ranges from about $-10°$ C. up to about 200° C.

13. A process for the production of a butene-1 rich stream containing not more than 0.1 ppm sulphur from a butene-containing $C_4$ hydrocarbon feed stream containing a minor amount of at least one sulphurous component selected from hydrogen sulphide, carbonyl sulphide, methyl mercaptan and mixtures of at least one thereof with at least one higher boiling sulphurous compound, which comprises providing a desulphurization zone maintained under desulphurization conditions and containing a charge of at least one solid desulphurization medium capable of converting to higher boiling sulphurous compounds by reaction with one or more components of the feed stream at least a portion of the hydrogen sulphide, carbonyl sulphide, and methyl mercaptan present in the feed stream and of absorbing or adsorbing substantially the remainder of any hydrogen sulphide, carbonyl sulphide and methyl mercaptan present in the feed stream, contacting the feed stream in the desulphurization zone with the solid desulphurization medium, passing thus treated feed stream, now essentially free from hydrogen sulphide, carbonyl sulphide and methyl mercaptan, to a distillation zone, recovering from the distillation zone a butene-2 rich stream and, as an overhead product, a butene-1 rich stream containing less than 0.1 ppm sulphur, and recovering substantially all of the higher boiling sulphurous compounds present in the treated feed stream in the bottoms product from the distillation zone.

* * * * *